United States Patent [19]
Ranford

[11] Patent Number: 5,176,658
[45] Date of Patent: Jan. 5, 1993

[54] VALVE ASSEMBLY FOR USE IN MEDICAL DEVICES

[75] Inventor: Alan B. Ranford, St. Louis, Mo.

[73] Assignee: Sherwood Medical Company, St. Louis, Mo.

[21] Appl. No.: 695,174

[22] Filed: May 3, 1991

[51] Int. Cl.⁵ .............................................. A61M 5/00
[52] U.S. Cl. .................................. 604/247; 137/102; 604/30
[58] Field of Search .................................. 604/30–31, 604/246–247; 137/102

[56] References Cited

U.S. PATENT DOCUMENTS

| | | | |
|---|---|---|---|
| 2,533,965 | 12/1950 | Schmohl et al. | 103/228 |
| 2,537,241 | 1/1951 | Smith | 103/150 |
| 2,576,894 | 11/1951 | Van Ranst et al. | 103/150 |
| 2,954,048 | 9/1960 | Rychlik | 137/512.15 |
| 3,084,707 | 4/1963 | Frye | 137/102 |
| 3,460,558 | 8/1969 | Johannisson | 137/102 |
| 3,957,052 | 5/1976 | Topham | 128/278 |
| 4,084,606 | 4/1978 | Mittleman | 404/30 X |
| 4,142,523 | 3/1979 | Stegeman | 128/214 R |
| 4,181,477 | 1/1980 | Litt | 417/560 |
| 4,210,173 | 7/1980 | Choksi et al. | 137/412.3 |
| 4,222,407 | 9/1980 | Ruschke et al. | 137/512.15 |
| 4,286,628 | 9/1981 | Paradis et al. | 137/843 |
| 4,445,535 | 5/1984 | Mayfield | 137/535 |
| 4,457,330 | 7/1984 | Fields | 137/102 |
| 4,461,313 | 7/1984 | Beaumont | 137/102 |
| 4,595,005 | 6/1986 | Jinotti | 128/205.24 |
| 4,646,781 | 3/1987 | McIntyre et al. | 137/512.4 |
| 4,921,488 | 5/1990 | Maitz et al. | 604/153 |

FOREIGN PATENT DOCUMENTS 2062116  7/1978  Fed. Rep. of Germany ...... 137/102

Primary Examiner—Michael H. Thaler
Assistant Examiner—C. Maglione
Attorney, Agent, or Firm—Andrew J. Beck; Montgomery W. Smith; Richard D. Allison

[57] ABSTRACT

A check valve assembly for use in medical devices having a single valve disc therein to allow a medical fluid to be drawn from a bulk container through the inlet opening and secondary opening of the valve assembly and into a syringe and then subsequently dispensing the fluid from the syringe through the secondary opening and outlet opening of the valve assembly and into a second container or to the patient. Alternately, the valve assembly may be used with a squeeze bulb of an aspiration device such that as the bulb is squeezed, the air in the bulb passes from the secondary opening to the outlet opening of the valve assembly and then, as the bulb is released, the negative pressure from the bulb is transmitted through the secondary opening and inlet opening of the valve assembly to the aspiration device to draw fluids from the patient and into the aspiration device.

19 Claims, 7 Drawing Sheets

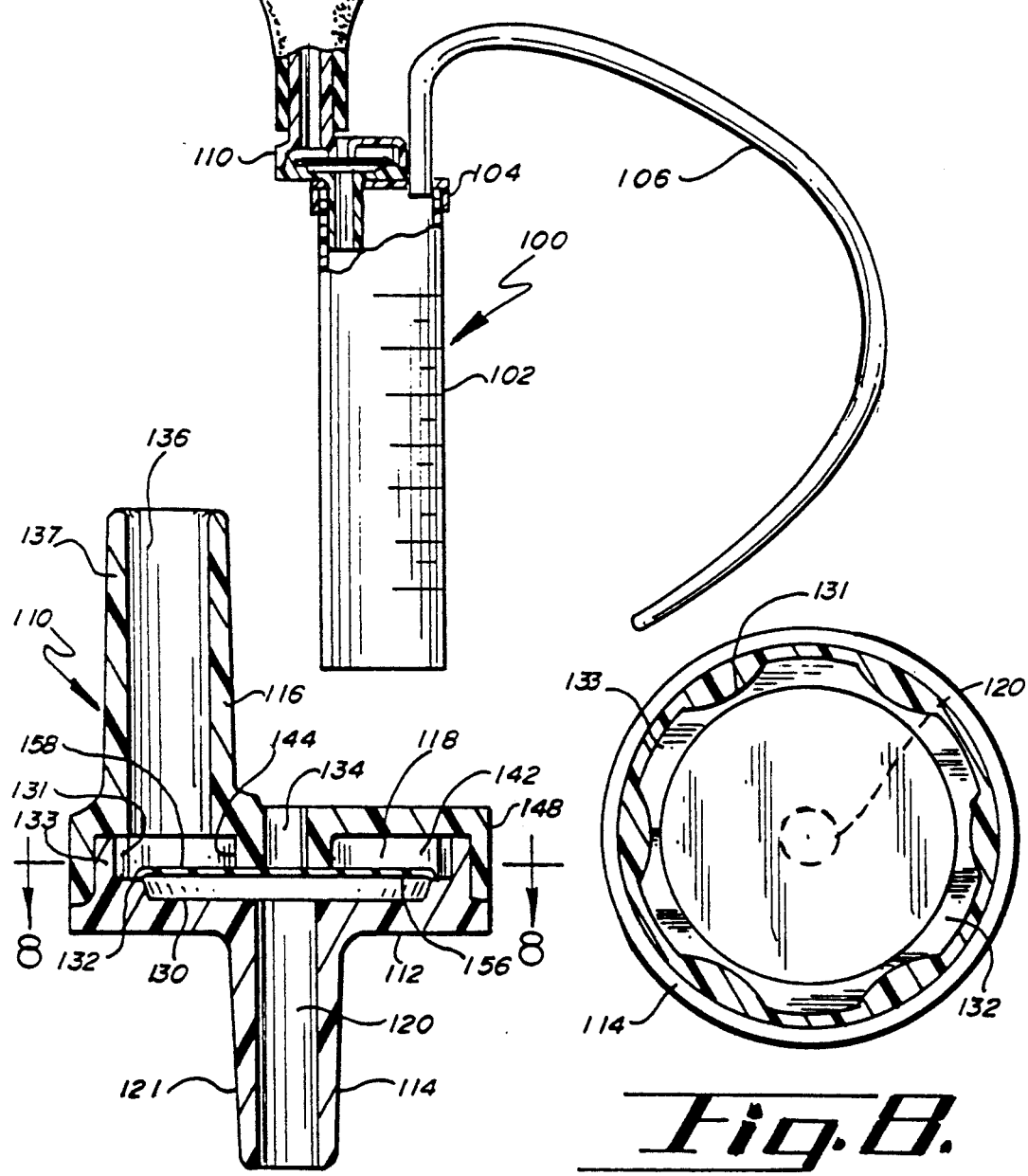

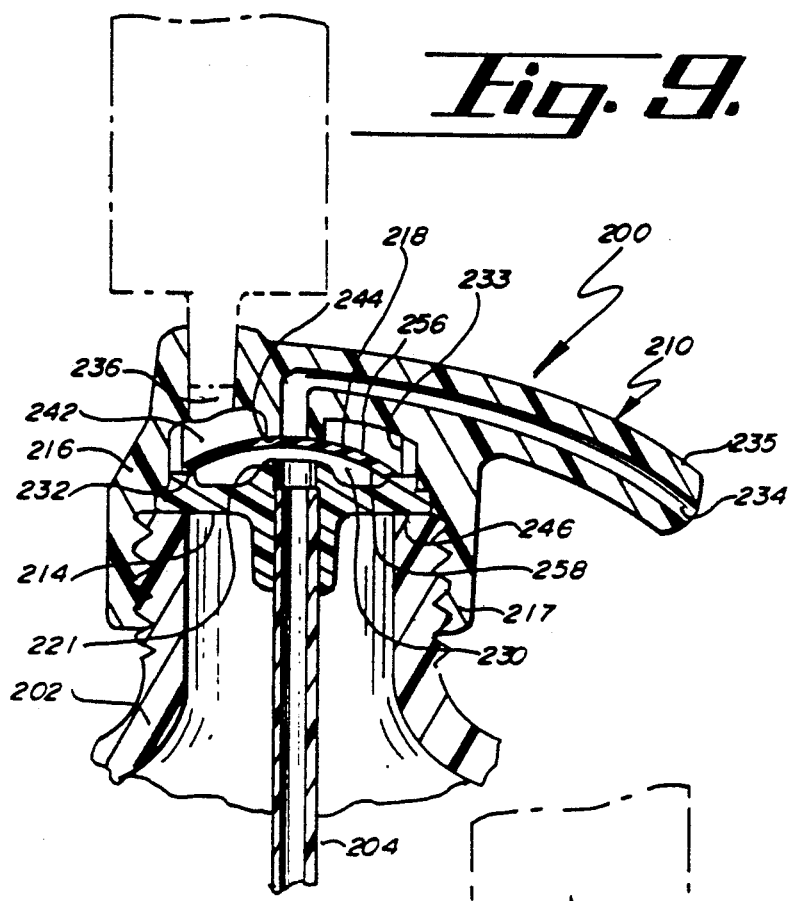

VALVE ASSEMBLY FOR USE IN MEDICAL DEVICES

FIELD OF THE INVENTION

The present invention relates to an improved check valve for use with a medical device wherein it is desired to transfer a controlled amount of medical fluid from a fluid reservoir to a medical device or patient or where it is desired to remove fluid from a patient using a manually operated medical device such as a squeeze bulb.

BACKGROUND OF THE INVENTION

In the field of medical devices, many medical devices utilize a connector having a pair of one-way valves therein. For example, in hospital pharmacies, it is oftentimes necessary to dilute or reconstitute a large number of medications. In order to expedite and reduce the cost of this procedure, a large bulk container of diluent, such as sterile water or normal saline, may be used. The bulk container is typically attached to a medical device having an inlet for the bulk container, a luer-type of connector for a syringe and an outlet which may be attached to a medication containing vial or an IV bag. These medical devices typically include a first one-way valve positioned between the inlet and the luer connector and a second similarly oriented one-way valve positioned between the luer connector and the outlet to enable the user to withdraw the desired amount of diluent from the bulk container into the syringe and then from the syringe into the vial or IV bag through the outlet of the medical device.

Variations of this medical device may also be used to transfer small amounts of fluid from a fluid reservoir into a medical device such as a closed system suction catheter to assist in the aspiration of the patient or to facilitate the removal of mucous from the interior and/or exterior of the catheter. Another use of a medical device having a pair of one-way valves positioned therein is illustrated in U.S. Pat. No. 4,921,488 granted to Maitz et al. The Maitz et al patent discloses the use of a squeeze bulb in combination with a meconium aspirator to remove meconium fluid from a baby during or shortly after delivery. The squeeze bulb disclosed in this patent includes a pair of one-way valves to allow the user to manually remove the air from the bulb when the bulb is squeezed and to apply a vacuum pressure to the aspirator when the bulb is released so that the fluids will be drawn from the patient into a collection device. In the Maitz et al. device, the one-way valves are usually constructed as flapper or duck bill type valves. These duck bill valves each consist of a pair of rubber members which are biased to close against each other as shown in the above-described Maitz et al. patent.

Another medical device which uses a pair of check valves is disclosed in U.S. Pat. No. 3,957,052 granted to Topham. In the Topham device, a pair of valve balls are used to selectively allow the flow of fluid between a needle and a syringe and then between the syringe and a container or collection vessel. The first valve ball of this device is movable between a first position adjacent to the opening of the syringe and a second position adjacent to the opening of the needle. In this device, when the first valve ball is in the first position, fluid is allowed to flow around the valve ball from the needle to the syringe. When the first valve ball is in the second position, fluid is prevented from flowing around the valve ball and into the needle. The second valve ball is retained adjacent to the opening of the container and is movable between open and closed positions.

Although the above described valves are adequate for most procedures, the use of two separate valves in each device increases the cost of the device and may also increase the likelihood that one of the valves may stick in either the open or closed position.

SUMMARY OF THE INVENTION

An object of the present invention is to overcome the disadvantages identified above by providing a relatively simple and inexpensive double check valve.

The present invention preferably consists of a two-piece molded valve housing having an inlet opening, a secondary opening and an outlet opening. A flexible valve disc is positioned in the valve housing so that either the inlet opening or the outlet opening is closed by the valve disc depending on whether or not fluid or air is being drawn out of or pushed into the secondary opening. As described more fully hereinafter, the valve disc is preferably freely positioned and slightly biased between the pieces of the valve housing so that the valve disc may readily press against the inside surface of either the inlet opening or the outlet opening. When fluid or air is drawn from the inlet opening to the secondary opening of the valve assembly, the center of the valve disc is forced against the inner surface of the outlet opening to form a seal therewith and prevent the flow of fluid or air through the outlet opening. Additionally, the peripheral surface of the valve disc flexes to allow the fluid or air to flow around the valve disc from the inlet opening to the secondary opening. When fluid or air is forced from the secondary opening to the outlet opening of the valve assembly, the center of the valve disc is forced against the inner surface of the inlet opening and the outer circumference of the valve disc is pressed against a raised circumferential ledge area on a portion of the valve housing to seal the inlet opening and prevent fluid or air from flowing to the inlet opening.

It is anticipated that the valve member may be used on nearly any medical device where a pair of one-way valves are presently being used. For example, the present invention is ideally suited for use in a hospital pharmacy or on closed system suction catheter as described above. With either of these uses, the fluid reservoir may be attached to the inlet opening and the vial, IV bag or catheter may be connected in flow communication with the outlet opening of the valve assembly. A syringe may be attached to the secondary opening of the valve assembly so that a precise amount of the fluid may be drawn into the syringe and then sterilely transferred from the fluid reservoir to whatever medical device is attached to the outlet opening of the valve assembly. Additionally, the present invention is also particularly useful in a squeeze bulb which may be adapted for use with an aspirator similar to the aspirator disclosed in the Maitz et al. patent described above. In this situation, the squeeze bulb is connected to the secondary opening of the valve assembly and the collection chamber of the aspirator is connected to the inlet opening of the valve assembly. When the squeeze bulb is squeezed, air is forced through the valve assembly and out of the outlet opening. As the squeeze bulb is reinflated, air is drawn from the collection chamber of the aspirator; through the inlet opening of the valve assembly and into the squeeze bulb to create a negative pressure in the collection chamber of the aspirator so that fluid is drawn into the collection chamber from the patient.

An advantage of the present invention is that it is simple and inexpensive to manufacture.

Yet another advantage of the present invention is that it is less likely to stick in either the open or closed position than prior devices because the valve disc is freely positioned in the valve assembly and is movable between a pair of flow restricting positions depending on whether or not fluid or air is being drawn into or expelled from the secondary outlet.

A further advantage of the present invention is that it may be used with many medical devices which previously required two separate one-way valve members.

BRIEF DESCRIPTION OF THE DRAWINGS

FIG. 6 is an elevated perspective view, partially in cross section, showing an alternate embodiment of the valve assembly of the present invention adapted for use with a manual aspiration device;

FIG. 7 is an enlarged cross-sectional view of the valve assembly shown in FIG. 6;

FIG. 8 is an enlarged cross-sectional view of the valve assembly shown in FIG. 6 taken generally along lines 8—8 of FIG. 7 with the valve disc removed therefrom;

FIG. 9 is an enlarged cross-sectional view of an alternate embodiment of the valve assembly of the present invention adapted for use on one type of fluid containing bottle;

FIGS. 10A and 10B are enlarged cross-sectional views of the alternate embodiment shown in FIG. 9 with a valve disc therein having a generally conically-shaped cross-section and wherein FIG. 10A illustrates the valve disc flexing the response to the user drawing fluid or air into the secondary opening and FIG. 10B illustrates the valve disc flexing in response to the dispensing of fluid or air from the secondary opening to the outlet opening of the alternate embodiment.

FIGS. 11A and 11B are enlarged cross-sectional views of another alternate embodiment of the present invention with a valve disc therein having a generally triangularly-shaped cross-section and wherein FIG. 11A illustrates the valve disc flexing in response to the user drawing fluid or air into the secondary opening of the valve assembly and FIG. 11B illustrates the valve disc flexing in response to the dispensing of fluid or air from the secondary opening of the alternate embodiment of the valve assembly.

DETAILED DESCRIPTION OF THE PREFERRED EMBODIMENT

The present invention is referred to herein in FIGS. 1-5 generally as a double check valve or valve assembly. The valve assembly of the present embodiment is designated herein generally as valve assembly 10.

As described herein, the terms "distal" or "distal end" are intended to refer to the surface or portion of a member or element closest to the outer surface of the outlet opening in the valve assembly 10 as described hereinafter. The terms "proximal" or "proximal end" are intended to define the surface or portion of a member or element which is located furthest from the outer surface of the outlet opening in the valve assembly 10 as described hereinafter.

As illustrated in FIGS. 1-5, the valve assembly 10 preferably consists of a cylindrically-shaped two-piece molded or otherwise formed valve housing 12 having first and second housing sections, 14 and 16, respectively. Additionally, a flexible valve disc 18 is freely retained within the valve housing 12 between the first and second housing sections, 14 and 16, as described hereinafter.

Figure 1:
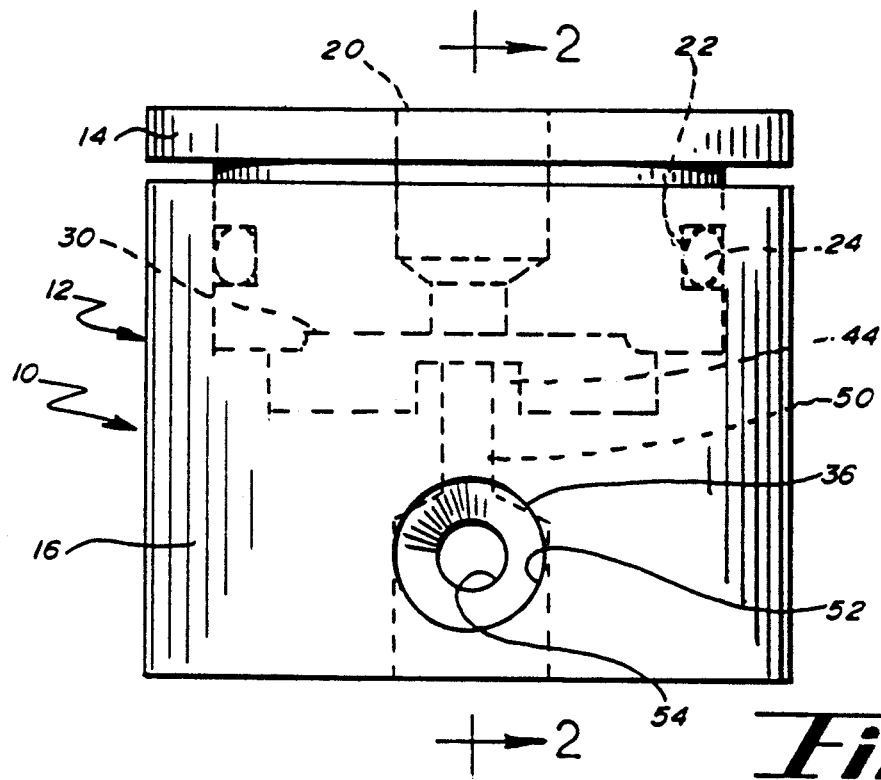
FIG. 1 is an elevated side view showing the secondary opening of the present invention.
Figure 2:
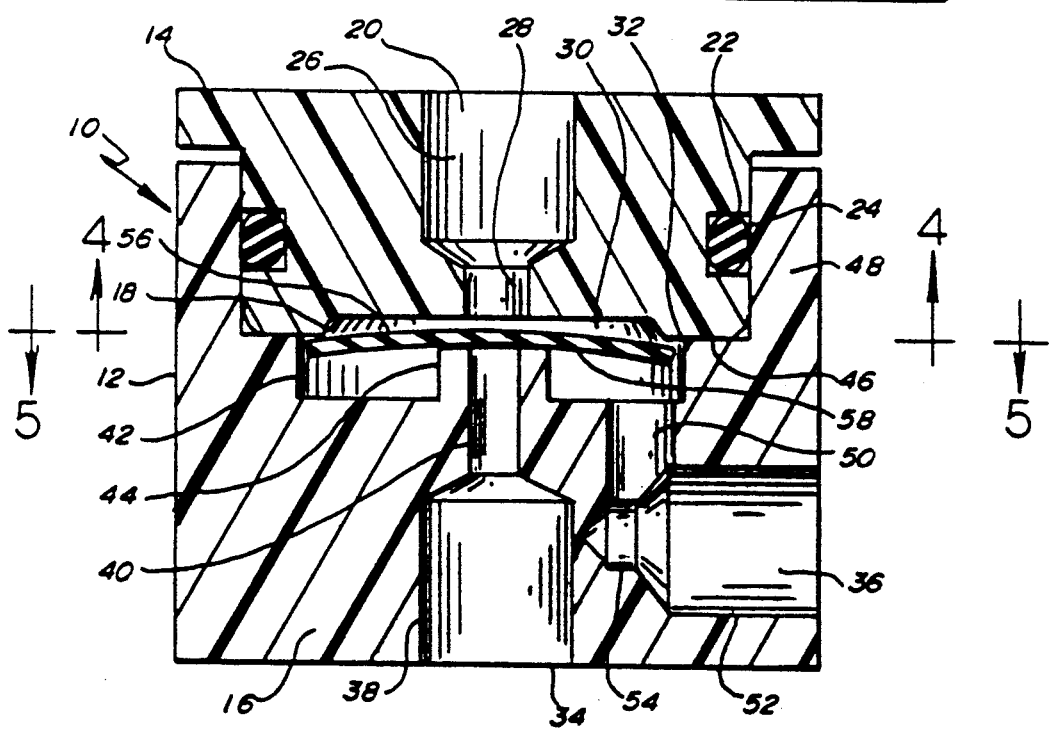
FIG. 2 is a cross-sectional view of the present invention taken generally along lines 2—2 of FIG. 1 showing the valve disc in a preloaded condition.

As shown in FIGS. 1-4, the first housing section 14 includes an inlet opening 20 and an annular recess 22 which is designed to receive an O-ring 24 therein to facilitate the attachment of the first housing section 14 to the second housing section 16 to form an air or fluid tight seal therebetween. As shown in FIG. 2, the inlet opening 20 of the present embodiment includes an enlarged diameter first inlet section 26 which is designed to receive an adaptor (not shown) therein and a smaller diameter second inlet section 28 which is located inwardly or distally of the first inlet section 26. The diameter and length of the second inlet section 28 is chosen to enable an adequate flow of fluid or air therethrough. The inner surface of the first housing section 14 preferably includes a recessed area 30 which is sized to allow the central portion of the valve disc 18 to be received therein while the outer circumference of the valve disc 18 is positioned against the raised ledge area 32 formed circumferentially about the recessed area 30 along the inner surface of the first housing section 14 as described more fully hereinafter.

As shown in FIGS. 1, 2, 3A, 3B and 5, the second housing section 16 includes an outlet opening 34 and secondary opening 36 therein. The outlet opening 34 extends from the outer surface of the second housing section 16 and includes a larger diameter first outlet section 38 and a proximally positioned smaller diameter second outlet section 40. The size and length of the first outlet section 38 is chosen to receive an adaptor therein. As with the second inlet section 28, the length and diameter of the second outlet section 40 is chosen to enable an adequate flow of fluid or air therethrough. In the present embodiment, the second outlet section 40 preferably has a diameter which is smaller than the diameter of the second inlet section 28, although it is anticipated that the present invention will operate satisfactorily if the diameter of the second inlet section 28 is the same or larger than the diameter of the second outlet section 40.

Figure 5:
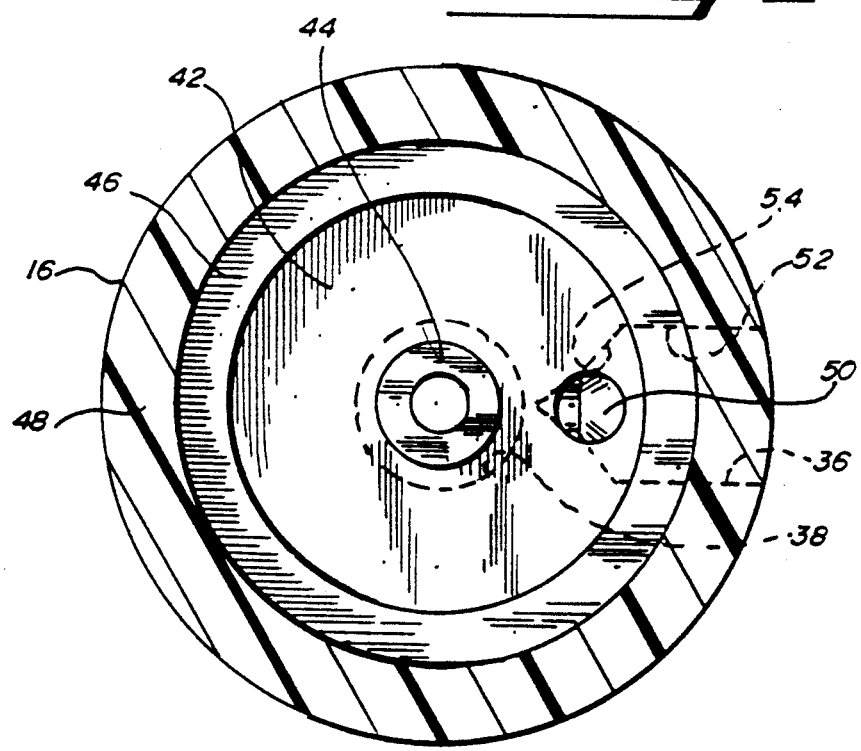
FIG. 5 is an elevated cross sectional view of the present invention taken generally along lines 5—5 of FIG. 2 with the valve disc removed therefrom.

As shown in FIGS. 2 and 5, the inner surface of the second housing section 16 includes a recessed area 42 thereon which is circumferentially larger than the recessed area 30 on the first housing section 14 and the circumference of the valve disc 18. Additionally, the recessed area 42 on the second housing section 16 is preferably recessed further inwardly than the recessed area 30 on the first housing section 14. The recessed area 42 on the second housing section 16 also includes a raised member 44 to selectively contact the valve disc 18 as described hereinafter. The raised member 44 is centrally positioned in the recessed area 42 and surrounds the inner surface of the outlet opening 34. The raised member 44 extends into the recessed area 42 to a level which will create the desired level of bias or preload on the valve disc 18 as described below. A ledge area 46 is formed circumferentially about the recessed area 42 on the second housing section 16. The ledge area 46 extends radially outwardly from the recessed area 42 to contact the ledge area 32 on the first housing section 14. A circumferential wall member 48 extends proximally from the ledge area 46 to sealingly contact the O-ring 24 and surround nearly the entire side surface of the first housing section 14.

As shown in FIG. 2, the secondary opening 36 of the preferred embodiment is oriented generally perpendicular to the outlet opening 34 on the second housing section 16 and includes a passageway 50 therein to provide flow communication between the secondary opening 36 and the recessed area 42. As with the inlet opening 20 and the outlet opening 34, the secondary opening 36 includes a reduced diameter second section 54 and an enlarged diameter first section 52 to allow the distal end of a syringe or other member to be received therein.

The valve disc 18 of the present embodiment is preferably a circular member constructed of a flexible, non-reacting material such as rubber. Although the valve disc 18 of the present embodiment is preferably a generally flat member, it is anticipated that the valve disc 18 may have a conical, triangular or other cross-sectional shape as described hereinafter. As shown in the drawings, the valve disc 18 is slightly biased or preloaded in the assembled valve assembly 10 to restrict the flow of fluid or air between the inlet opening 20, the secondary opening 36 and the outlet opening 34 as described more fully hereinafter. Additionally, the valve disc 18 is preferably freely positioned in the valve housing 12 such that the valve disc 18 is preferably not bonded or otherwise fixedly attached to any surface in the valve housing 12. The valve disc 18 includes a proximal surface 56 which faces the inner surface of the inlet opening 20 and the recessed area 30 of the first housing section 14 and a distal surface 58 which faces the inner surface of the outlet opening 34 and the recessed area 42 of the second housing section 16. The diameter of the valve disc 18 is chosen so that the outer circumference or periphery of the valve disc 18 contacts the ledge area 32 on the first housing section 14 in the preload condition or when fluid or air passes between the outlet opening 34 and the secondary opening 36 as described hereinafter. The flexibility and amount of preload applied to the valve disc 18 is chosen so that the outer circumference of the valve disc 18 flexes away from the ledge area 32 on the first housing section 14 and the distal surface 58 of the valve disc 18 seals the inner surface of the outlet opening 34 when fluid or air passes between the inlet opening 20 and the secondary opening 36 as described below.

When the valve assembly 10 of the present embodiment is assembled, the valve disc 18 is freely retained in a preloaded condition within the recessed areas, 30 and 42, of the first and second body sections, 14 and 16. As shown in FIG. 2, the outer periphery of the valve disc 18 rests against the ledge area 32 on the first body section 14 and the center of the valve disc 18 rests against the raised member 44 on the second housing section 16 when the valve disc 18 is in the preloaded condition.

Figure 3A:
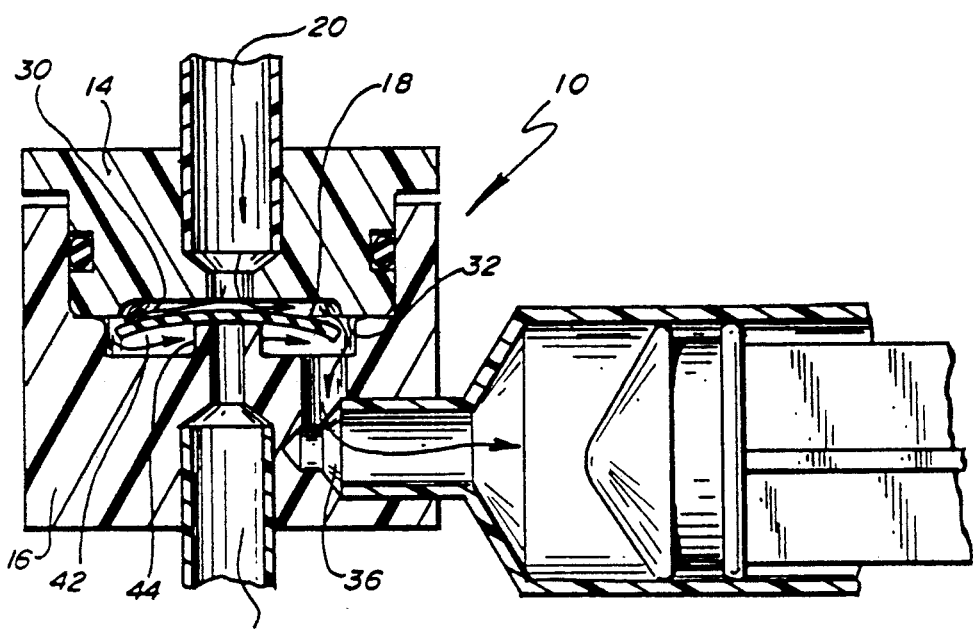
FIG. 3A is a cross-sectional view of the present invention taken generally along lines 2—2 of FIG. 1 showing the valve disc flexed to allow the flow of fluid or air between the inlet opening and the secondary opening of the valve assembly with a syringe and tubing attached to the valve assembly.

If the present embodiment is used to transfer fluid from a bulk container to a syringe, the bulk container may be attached to the inlet opening 20 and a syringe may be inserted into the secondary opening 36 in the valve assembly 10. As shown in FIG. 3A, when the plunger rod of the syringe is withdrawn, the fluid will contact the proximal surface 56 of the valve disc 18 and the pressure differential between the proximal and distal surfaces, 56 and 58, of the valve disc 18 will press the center of the valve disc 18 against the raised member 44. This contact between the valve disc 18 and the raised member 44 prevents the flow of fluid or air between the distal surface 58 of the valve disc 18 and the outlet opening 34. The incoming fluid and the resulting pressure differential will also flex the outer circumference of the valve disc 18 away from the ledge area 32 on the first housing section 14 to allow the flow of fluid through both recessed areas 30 and 42 and into the secondary opening 36. The use of the O-ring 24 and annular recess 22 on the first housing section 14 and the close fit between the first housing section 14 and the second housing section 16 prevent the leakage of air or fluid from the interior of the valve assembly 10.

Figure 3B:
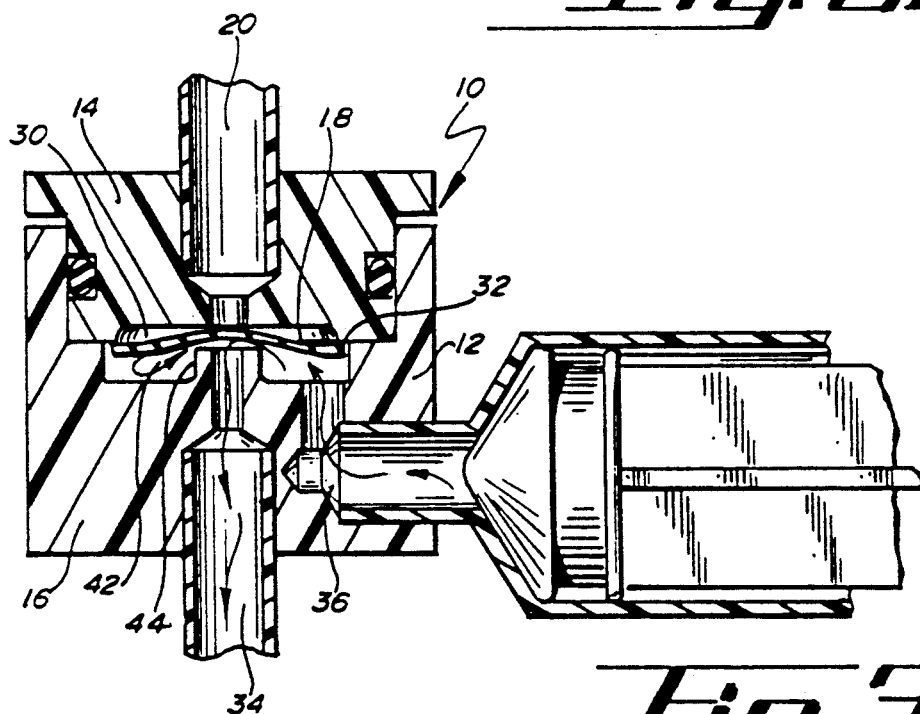
FIG. 3B is a cross-sectional view of the present invention taken generally along lines 2—2 of FIG. 1 showing the valve disc flexed to allow the flow of fluid or air between the secondary opening and the outlet opening of the valve assembly with a syringe and tubing attached to the valve assembly.
Figure 4:
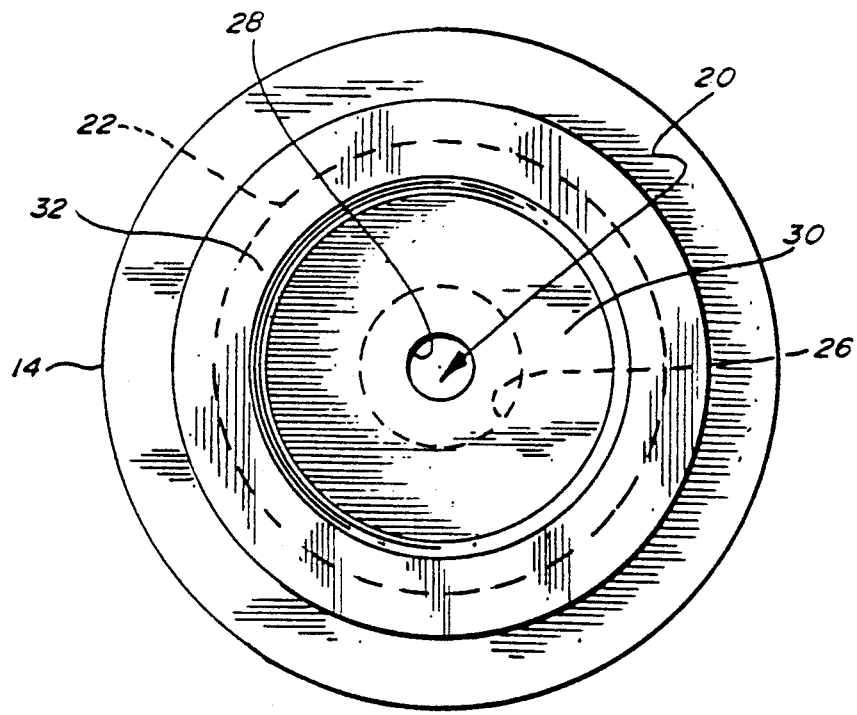
FIG. 4 is an elevated cross-sectional view of the present invention taken generally along lines 4—4 of FIG. 2.

When the user desires to transfer the measured amount of fluid from the syringe to the medication vial or other receptacle, the flow of fluid from the secondary opening 36 to the outlet opening 34 will create a pressure differential between the proximal and distal surfaces, 56 and 58, of the valve disc 18 to cause the valve disc 18 to flex and prevent the flow of fluid through the inlet opening 20, as shown in FIG. 3B. As the fluid is dispensed from the syringe through the valve assembly 10, the fluid flows through the secondary opening 36 and passageway 50 to contact the distal surface 58 of the valve disc 18. As this occurs, the resulting pressure differential forces the outer periphery of the valve disc 18 against the ledge area 32 to prevent the flow of fluid between the proximal surface 56 of the valve disc 18 and the ledge area 32. Additionally, the difference in pressure between the proximal and distal surfaces, 56 and 58, of the valve disc 18 cause the center of the valve disc 18 to press against the inner surface of the inlet opening 20 to further prevent the flow of fluid therethrough. As the center of the valve disc 18 is moved against the inlet opening 20 on the first housing section 14, fluid is allowed to flow around the raised member 44 on the second housing section 16 and into the outlet opening 34.

FIGS. 6-8 illustrate another embodiment of the present invention adapted for use with an aspirator generally of the type described in U.S. Pat. No. 4,921,488 (incorporated herein by reference). The aspirator 100 of this embodiment generally includes a cylindrically shaped fluid collector 102 having a cover 104 thereon to define an air-tight chamber for receiving aspirated body fluids therein, and an elongated flexible tube 106 which is operatively connected at one end to the fluid collector 102 and has a free end which is adapted to be inserted into the mouth or other opening of the patient to remove fluids therefrom. Additionally, the aspirator 100 includes a squeeze bulb 108 having a valve assembly 110 inserted in the open end thereof. The valve assembly 110 is operatively connected between the squeeze bulb 108 and the cover 104 of the fluid collector 102. As best shown in FIG. 7, this embodiment of the present invention consists of a preferably cylindrically shaped and molded two-piece valve housing 112 having first and second housing sections, 114 and 116 respectively, with a generally flat valve disc 118 freely positioned and slightly biased in a preloaded condition between the first and second housing sections, 114 and 116. As stated above with respect to the prior embodiment, the valve disc 118 of the present embodiment may also be formed as generally conical or triangularly-shaped member without materially affecting the operation of the present embodiment.

As shown in FIGS. 6 and 7, this embodiment includes first and second housing sections 114 and 116, respectively. As described above, the terms "distal" or "proximal" are used herein with respect to the relative position of the member to the outlet opening of the present invention. The proximally positioned inlet opening 120, as defined herein, extends through the first housing section 114. The inlet opening 120 includes an elongated cylindrical attachment member 121 extending from the proximal side of the valve assembly 110 to enable the valve assembly 110 to be attached directly to the cover 104 of the fluid collector 102 or to a short flexible tubular member (not shown) which is subsequently attached to the cover 104 of the fluid collector 102. As with the prior embodiment, the inner surface of the first housing section 114 includes a recessed area 130 which extends along nearly the entire inner surface of the first housing section 114 and a ledge area 132 which circumferentially surrounds the recessed area 130. Additionally, as shown in FIG. 8, a plurality of spaced apart positioning ribs 131 on the first housing section 114 extend inwardly from a distally extending wall member 133 to assist in aligning the valve disc 118 within the valve housing 112 as described hereinafter.

The distally positioned second housing section 116 of this embodiment includes the outlet opening 134 and the secondary opening 136 extending therethrough. As with the prior embodiment, the inner surface of the second housing section 116 includes a recessed area 142 and raised member 144 which surrounds the outlet opening 134. The raised member 144 is sized to contact the distal surface 158 of the valve disc 118 as described hereinafter. As shown in FIG. 7, the outer surface of the outlet opening 134 is flush with the distal surface of the second housing section 118 and is open to the atmosphere. The secondary opening 136 includes a distally extending elongated and generally cylindrical attachment member 137 to facilitate the attachment of the squeeze bulb 108 to the valve assembly 110 as shown in FIG. 6.

The valve disc 118 of the present embodiment is a preferably circular member constructed of a flexible, nonreacting material such as rubber. The valve disc 118 includes a proximal surface 156 which faces the inner surface of the first housing section 114 and a distal surface 158 which faces the inner surface of the second housing section 116. The outer periphery of the valve disc 118 is designed to contact the ledge area 132 of the first housing section 114 when the valve disc 118 is in the preloaded condition within the valve assembly 110 as shown in FIG. 7. When the valve assembly 110 of the present embodiment is assembled, the valve disc 118 is freely retained and slightly biased within the recessed areas, 130 and 142, of the first and second housing sections 114 and 116. It is anticipated that the first and second housing sections 114 and 116 may be frictionally, adhesively or otherwise bonded together to form an air and fluid tight seal between the wall member 133 on the first housing section 114 and the circumferential wall member 148 on the second housing section 116. The wall member 133 and positioning ribs 131 on the first housing section 114 retain the valve disc 118 centrally positioned in the recessed areas 130 and 142. As shown in FIG. 8, when the valve disc 118 is in the slightly biased or preloaded condition, the distal surface 158 of the valve disc 118 rests on the proximal end of the centrally-positioned raised member 144 and the proximal surface 156 of the periphery of the valve disc 118 rests on the ledge area 132 of the first housing section 114.

When the user squeezes the squeeze bulb 108 on the aspirator 100, air is forced into the valve assembly 110 and through the secondary opening 136 by creating a pressure differential between the proximal and distal surfaces, 156 and 158, of the valve disc 118. As the air is forced into the secondary opening 136, the outer periphery of the valve disc 188 is forced against the ledge area 132 on the first housing section 114 by the pressure differential between the proximal and distal surfaces, 156 and 158, of the valve disc to prevent the flow of air therebetween. Additionally, the central portion of the valve disc 118 is moved away from the raised member 144 on the second housing section 116 and pressed against the inner surface of the inlet opening 120 to allow air to flow from the secondary opening 136 to the outlet opening 134. As the pressure on the squeeze bulb log is released, a negative pressure is created in the squeeze bulb 108 and transmitted through the valve assembly 110 to the fluid collector 102 and flexible tube 106. When this occurs, the outer periphery of the valve disc 118 is drawn away from the ledge area 132 on the first housing section 14 by the resulting pressure differential between the proximal and distal surfaces, 158 and 156, of the valve disc 118 to allow air to flow therebetween. Additionally, the flow of air from the inlet opening 120 causes the center portion of the valve disc 118 to press against the inner surface of the raised member 144 to seal the outlet opening 134. The negative pressure created by the release of pressure on the squeeze bulb 108 causes fluid or mucous from the patient to be drawn through the flexible tube 106 and into the fluid collector 102.

Figure 10B:
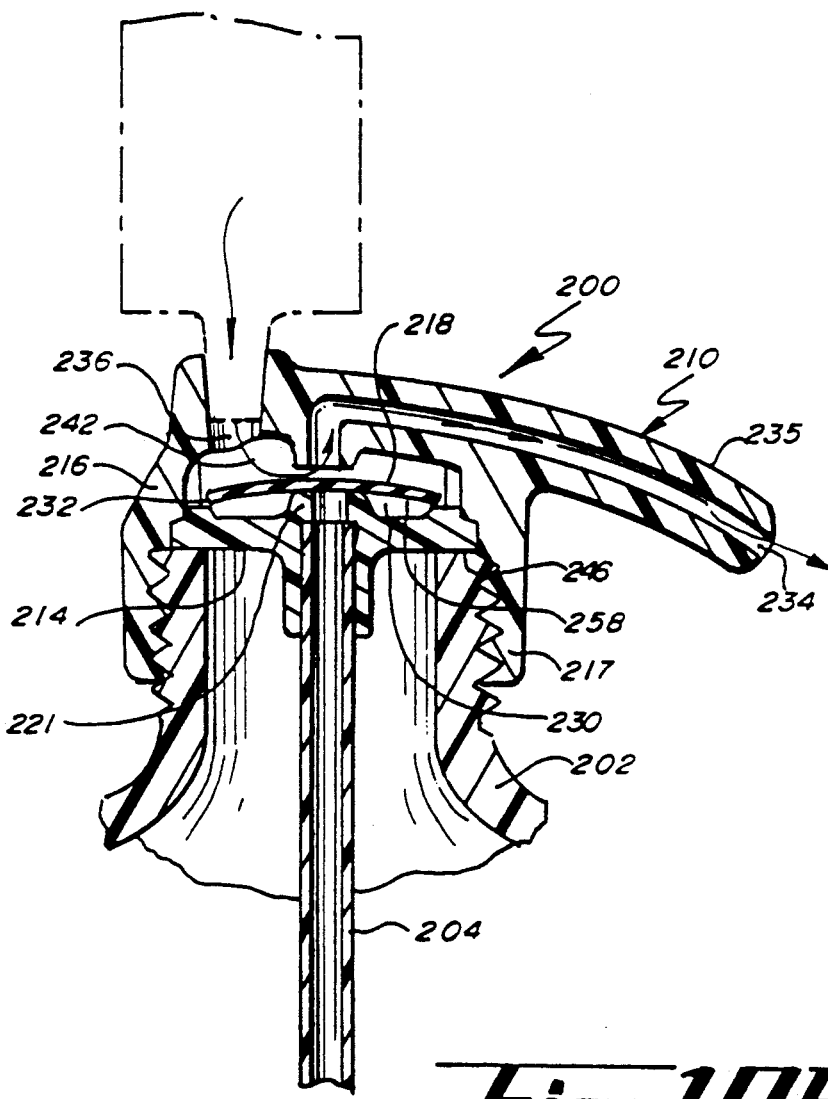

FIGS. 9, 10A and 10B illustrate another form of the present invention adapted for use with one type of fluid containing bottle 202 to dispense a measured amount of fluid from the bulk storage bottle. Although the present embodiment is illustrated and described herein as being attached to a fluid containing bottle having a tube 204 therein to draw fluids from the bottom of the bottle 202, it is anticipated that this embodiment may be used on other fluid containing bottles or containers by merely inverting the bottle or container so that the tube 204 may be eliminated. As shown in FIG. 9, the fluid delivery assembly 200 includes a threaded fluid containing bottle 202 and valve assembly 210.

In this embodiment, the proximally positioned first housing section 214 of the valve housing 212 also functions to support the tube 204 in the bottle 202. Additionally, the bottle 202 is threadedly connected to the valve assembly 210 and a syringe may be connected to the distally positioned secondary opening 236 of the valve assembly 210.

The distally positioned second housing section 216 includes the secondary opening 236 and an outlet opening 234 extending therethrough. In this embodiment, the secondary opening 236 preferably has tapered sidewalls to receive a luer-lock type of syringe therein. The outlet opening 234 of this embodiment includes an elongated and cylindrical wall member 235 which extends laterally from the side of the valve assembly 210 to facilitate the dispensing of a measured amount of fluid therefrom. The second housing section 216 also includes a proximally extending wall member 217 having internal threads thereon. The internal threads on the wall member 217 are adapted to engage the external threads on the bottle 202. A circumferential ledge area 246 is positioned distally and radially inwardly of the internal threads to engage the outer periphery of the first housing section 214 which is welded, bonded or otherwise attached thereto to form a fluid-tight seal therebetween as described hereinafter. As with the prior embodiment, the present embodiment also includes a plurality of spaced apart positioning ribs 233 on the second housing section 216 which are positioned inwardly and distally of the ledge area 246 to retain the valve disc 218 in position within the recessed areas 230 and 242. The inner surface of the second housing section 216 includes a recessed area 242 therein which is recessed further than the recess area 230 in the first housing section 214. A raised member 244 circumferentially surrounds the outlet opening 234 and extends further proximally into the recessed area 242 than the laterally offset secondary opening 236.

As described briefly above, the first housing section 214 supports the tube 204 in the bottle 202 and is retained in positioned on the top of the bottle adjacent to the ledge area 246 on the second housing section 216. The inner surface of the first housing section 214 of this embodiment includes a recessed area 230 having a centrally positioned and distally extending raised member 221 therein. A circumferential ledge area 232 surrounds the recessed area 230 and is sized such that the raised member 221 extends distally of the ledge area 232.

As shown in FIGS. 9, 10A and 10B, the valve disc 218 of this embodiment preferably consists of a flexible rubber member. As shown in FIG. 9, the valve disc 218 has a slightly conically-shaped cross-section and, in the initial preloaded position, the central portion of the valve disc 218 is biased against the raised member 244 so that the proximal surface 256 of the valve disc 218 seals against the outlet opening 234 and the peripheral portion of the valve disc 218 is biased against the ledge ar a 232 on the first housing section 214 so that the valve disc 218 isolates the inlet opening 220 from communication with the outlet opening 234.

As with the prior embodiments, the first housing section 214 and second housing section 216 of this embodiment may be pre-assembled with the valve disc 218 slightly biased in the preloaded condition therebetween so that the entire valve assembly 210 may be threadedly attached to the bottle 202. The tube 204 may also be packaged separately so that if the bottle is to be inverted (not shown) the tube 204 need not be used but if it is necessary for the bottle 202 to be in an upright position, the tube 204 may be inserted into the inlet opening 220 of the valve assembly 210 prior to use.

As shown in FIGS. 10A and 10B, the valve disc 218 of the present embodiment, selectively controls the flow of fluid between the inlet opening 220 and the outlet opening 234 of the valve assembly 210. When the user desires to obtain a measured amount of fluid from the bottle 202, the user withdraws the plunger rod in the syringe so that a pressure differential is created between the proximal and distal surfaces, 256 and 258, of the valve disc 218 as fluid is drawn into the valve assembly 210 through the tube 204. As this occurs, the fluid contacts the proximal surface 256 of the valve disc 218 and the pressure differential between the proximal surface 256 and the distal surface 258 of the valve disc 218 causes the outer periphery of the valve disc 218 to move away from the ledge area 232 to allow the fluid to flow therebetween. The force applied to the face of the raised member 244 by the distal surface 258 of the valve disc 218 by virtue of the preload of the valve disc 218 must be sufficient to overcome the force created by the pressure differential acting on the circumference of the distal surface 258 of the valve disc 218 by virtue of the preload of the valve disc 218 must be sufficient to overcome the force created by the pressure differential acting on the circumference of the distal surface 258 of the valve disc 218 caused by the withdrawal of the plunger rod in the syringe barrel to maintain the sealing contact between the valve disc 218 and the raised member 244 while allowing fluid to flow around the outer periphery of the valve disc 218.

When the fluid is to be expelled from the syringe and into the bottle or container, the pressure differential between the distal and proximal surfaces, 256 and 258, of the valve disc 218 is reversed. This pressure differential allows the fluid to pass through the secondary opening 236 and flow along the distal surface 258 of the valve disc 218 while the outer periphery of the valve disc 218 sealingly contacts the ledge area 232 on the first housing section 214 to prevent the flow of fluid therebetween. Additionally, the pressure differential between the proximal and distal surfaces 256 and 258 of the valve disc 218 cause the distal surface 258 of the valve disc 218 to move away from the raised member 244 to allow the fluid to flow into the outlet opening 234 of the valve assembly 210.

Figure 11A:
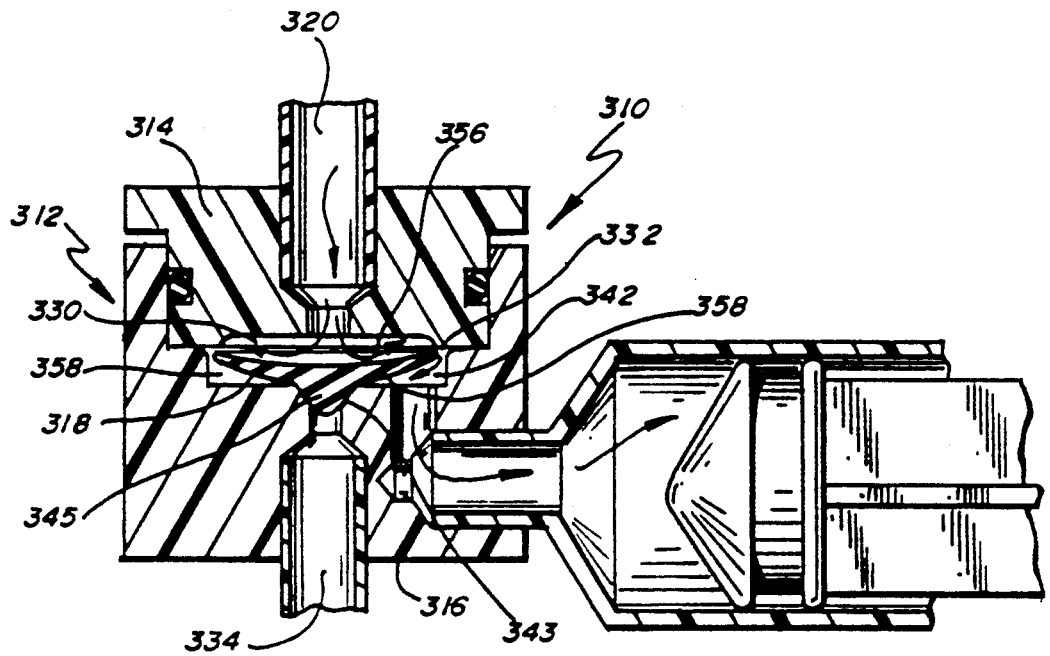
Figure 11B:
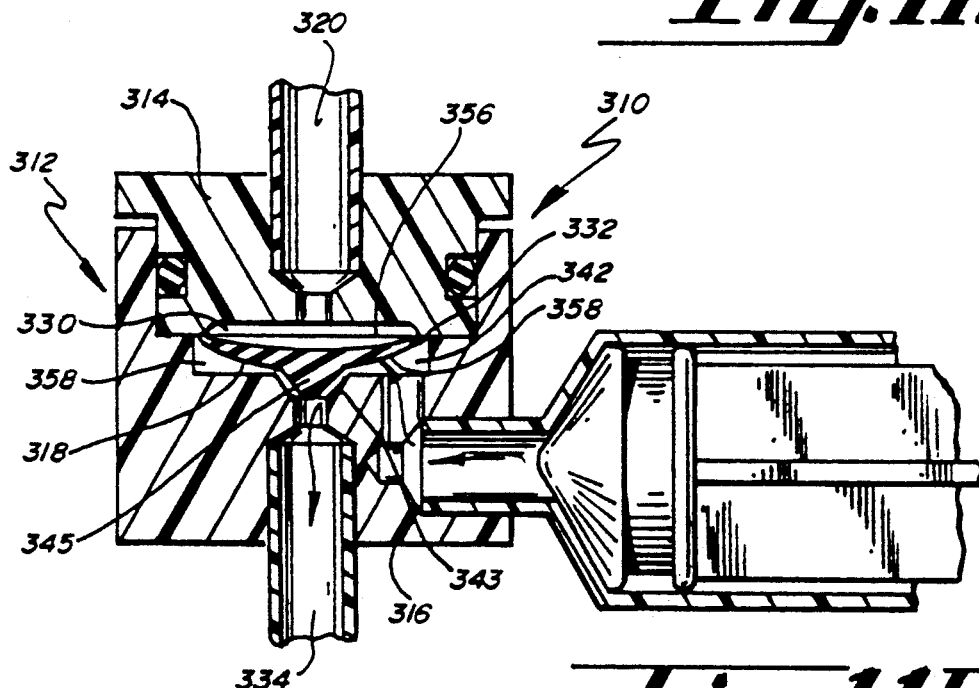

FIGS. 11A and 11B illustrate yet another embodiment of the present invention wherein the valve disc 318 has a generally conical shape and is slightly flexed in the preloaded condition. As shown in the drawings, the valve housing 312 of the valve assembly 310 is nearly identical to the valve housing 12 shown in FIGS. 1-5 and described above with respect to the prior embodiment. The inlet opening 320, secondary opening 336 and outlet opening 334 are oriented on the valve housing 312 in the same manner as described above with respect to the prior embodiment. The first housing section 314 includes an inner recessed area 330 which is circumferentially surrounded by a ledge area 332 and the second housing section 316 includes an inner surface having a recessed area 342 that is larger than the recessed area 332 on the first housing section 314. Unlike the prior embodiments, there are no raised members extending into the recessed areas 330 or 342 of the valve housing 312. Additionally, the recessed area 342 on the second housing section 316 preferably includes a proximally tapered section 343 which is adapted to receive a similarly-shaped tapered portion 345 of the preloaded valve disc 318 therein as described hereinafter.

As shown in FIG. 11A, when the user desires to draw fluid or air through the valve assembly 310, the pressure differential between the proximal surface 356 and the distal surface 358 of the valve disc 318 causes the peripheral edge of the valve disc 318 to move distally in the recessed areas 330 and 342 of the valve housing 312 and move away from the ledge area 332 on the first housing section 314. The pressure differential in the valve assembly 310 also causes the tapered portion 345 of the valve disc 318 to enter and form a fluid-tight seal with the tapered section 343 of the second housing section 316.

As shown in FIG. 11B, when the user desires to dispense the fluid or air through the valve assembly 310, a second pressure differential is created between the proximal and distal surfaces, 356 and 358, of the valve disc 318. This second pressure differential flexes the valve disc 318 so that the valve disc 318 moves proximally in the recessed areas 330 and 342 of the valve housing 312 so that the tapered portion 345 of the valve disc 31 is spaced apart from the tapered section 343 of the second housing section 316 to allow the fluid or air to flow therebetween. The pressure exerted by the fluid or air on the distal surface 358 of the valve disc 318 also cause the outer periphery of the distal surface 356 of the valve disc 318 to sealingly contact the ledge area 332 on the first housing section 314.

It is anticipated that the valve disc and valve housing as described above in the various embodiments of the present invention may be constructed of a variety of materials having various shapes and sizes without departing from the intended scope of the present invention. Additionally, it is anticipated that the valve assembly of the present invention may be used with other medical devices or in other medical procedures without departing from the intended scope of the present invention as defined by the following claims.

What is claimed is:

1. A medical device for use with a valve assembly wherein said medical device comprises:
   a valve means having proximal and distal surfaces;
   a housing assembly having said valve means freely retained in an initial biased position therein, said housing assembly including an inlet opening, a secondary opening and an outlet opening therein wherein said inlet opening and said secondary opening are adapted to be in flow communication in a first position of said valve mans and said secondary opening and said outlet opening are adapted to be in flow communication in a second position of said valve means; and
   wherein a pressure means is operatively associated with said secondary opening and a fluid receiving aspiration means is operatively associated with said inlet opening such that when excess pressure is created by said pressure means, said valve means is moved to said second position and when negative pressure is crated by said pressure means, said valve means is moved to said first position.

2. The medical device of claim 1 wherein direct flow communication between said inlet opening and said outlet opening is prevented by said valve means.

3. The medical device of claim 1 wherein said valve mean is movably positioned in said housing assembly and said distal surface of said valve means operatively obstructs flow communication through said outlet opening when said valve means is in said first position and wherein said proximal surface of said valve means operatively obstructs flow communication through said inlet opening when said valve means is in said second position.

4. The medical device of claim 1 wherein said housing assembly includes at least first and second housing sections wherein said first and second housing sections have distal and proximal surfaces and said distal surface of said first housing section and said proximal surface of said second housing section are operatively positioned adjacent each other and wherein said distal surface of said first housing section includes a first recessed area in flow communication with said inlet opening and said proximal surface of said second housing section includes a second recessed area in flow communication with said outlet opening and wherein said valve means is operatively positioned in at least one of said first or second recessed areas.

5. The medical device of claim 1 wherein said housing assembly includes a recessed area therein and said valve means is operatively positioned in said recessed area in said housing assembly and includes a central portion and a peripheral portion wherein said central portion obstructs flow communication through said outlet opening in said fist position of said valve means and said peripheral portion obstructs flow communication through said inlet opening in said second position of said valve means.

6. A medical device for the aspiration of fluids from a patient, the medical device comprising:
   a flexible valve means having distal and proximal surfaces;
   a housing assembly having said valve means operatively positioned therein a nd including an inlet opening, a secondary opening and an outlet opening therein in operative communication with said valve means and wherein said valve means is alternately movable between first and second positions wherein said valve means obstructs the flow of air through said outlet opening and allows the flow of air between said inlet opening and said secondary opening in said first position and said valve means obstructs the flow of air through said inlet opening and allows the flow of said between said secondary opening and said outlet opening in said second position; and
   wherein a pressure means is operatively associated with said secondary opening and a fluid receiving aspiration means is operatively associated with said inlet opening such that when excess pressure is created by said pressure means, said valve means is moved to said second position and when negative pressure is created by said pressure means, said valve means is moved to said first position.

7. A valve assembly adapted for use with a medical device wherein said valve assembly comprises:
   a valve disk having a conically shaped cross-section and proximal and distal surfaces;
   a housing assembly having said valve disk freely retained in an initial preloaded condition therein, said housing assembly including an inlet opening, a secondary opening and an outlet opening therein wherein said inlet opening and said secondary opening are adapted to be in flow communication in a first position of said valve disk and second secondary opening and said outlet opening are adapted to be in flow communication in a second position of said valve disk; and
   wherein said inlet opening is adapted to be operatively associated with a source of fluid or air and said secondary opening is adapted to be operatively associated with a fluid or air dispensing means and said outlet opening is adapted to be operatively associated with a receiving means such that said valve disk alternately obstructs the flow of fluid or air between said outlet opening said secondary opening and said inlet opening and said secondary opening.

8. The valve assembly of claim 7 wherein said dispensing means is a syringe means adapted to alternately receive fluid therein from said inlet opening and dispense fluid therefrom through said outlet opening.

9. The valve assembly of claim 7 wherein said dispensing means is a pressure means adapted to alternately dispense air therefrom through said outlet opening and apply a negative pressure through said inlet opening.

10. A valve assembly adapted for use with medical devices, the valve assembly comprising:
  a housing assembly having an exterior surface with an inlet opening, a secondary opening and an outlet opening, said housing assembly further including a recessed area therein a flow communication with said openings,; and
  a valve disk having a conically shaped cross-section and distal and proximal surfaces wherein said valve disk is freely retained in an initial biased position in said recessed area and a first section of said inlet opening is operatively positioned adjacent said proximal surface f said valve disk and said secondary opening and said outlet opening are operatively positioned adjacent said distal surface of said valve disk.

11. The valve assembly of claim 10 wherein said valve disk is alternately movable between first and second positions wherein flow communication through said outlet opening is obstructed in said first position and flow communication through said inlet opening is obstructed in said second position.

12. The valve assembly of claim 11 wherein said valve disk comprises a flexible member sized to be received within said recessed area and wherein said recessed area includes a ledge area circumferentially surrounding a portion of said recessed area such that a portion of said flexible member contacts said ledge area in said second position and is spaced apart from said ledge area in said first position.

13. The valve assembly of claim 11 wherein said valve disk comprises a flexible member sized to be freely received in said recessed area and wherein said distal surface of said flexible member is biased to contact and obstruct flow through said outlet opening when said flexible member is in said fist position.

14. The valve assembly of claim 10 wherein said valve disk is sized to be received in said recessed area and said valve disk has a generally conically-shaped cross-section wherein said distal surface of said valve disk is adapted to be spaced apart from said outlet opening in a second position of said valve disk and wherein flow communication through said outlet opening is obstructed by an apex on said distal surface of said valve disk in a first position of said valve disk.

15. A medical device for the delivery of medical fluid from a bulk container, the medical device comprising:
  a flexible valve disk having a conically shaped cross-section and distal and proximal surfaces, and
  a housing assembly having said valve disk operatively positioned therein and including an inlet opening, a secondary opening and an outlet opening therein in operative communication with said valve means and wherein said valve disk is freely retained in an initial biased position in said housing assembly and movable between first and second positions wherein said valve disk obstructs the flow of fluid through said outlet opening and allows the flow of fluid between said inlet opening and said secondary opening in said fist position and obstructs the flow of fluid through said inlet means and allows the flow of fluid between said secondary opening and said outlet opening in said second position.

16. A medical device for the delivery of medical fluid from a bulk container, the medical device comprising:
  a flexible valve disk having a generally conical shaped cross-section and distal and proximal surfaces, and
  a housing assembly having said valve disk operatively positioned therein and including an inlet opening, a secondary opening and an outlet opening therein in operative communication with said valve means and wherein said valve disk is freely retained in an initial preloaded condition in said housing assembly and movable between first and second positions wherein said valve disk obstructs the flow of fluid through said outlet opening and allows the flow of fluid between said inlet opening and said secondary opening in said first position and obstructs the flow of fluid through said inlet means and allows the flow of fluid between said secondary opening and said outlet opening in said second position; and
  wherein a syringe means is operatively associated with said secondary opening and wherein said valve disk is in said first position as fluid is drawn into said syringe means and said valve disk is in said second position as fluid is expelled from said syringe means.

17. The medical device of claim 16 wherein said valve disk is a flexible member freely positioned in said housing assembly and wherein said inlet opening is oriented operatively adjacent said proximal surface of said valve disk and said outlet opening is oriented operatively adjacent said distal surface of said valve disk such that said valve disk is flexed to allow fluid to flow around at least a portion of said valve disk as fluid is drawn into said syringe means and the flow of fluid is prevented from flowing around said valve disk as fluid is expelled from said syringe means.

18. The medical device of claim 16 wherein said housing assembly includes a recess therein and said secondary opening is operatively positioned adjacent said distal surface of said valve disk and said valve disk is freely positioned in a preloaded condition in said recess in said housing assembly.

19. A valve assembly adapted for use with a medical device wherein said valve assembly comprises:
  a valve means having proximal and distal surfaces;
  a housing assembly having said valve means operatively associated therewith, said housing assembly including an inlet opening, a secondary opening and an outlet opening therein wherein said inlet opening and said secondary opening are adapted to be in flow communication in a first position of said valve means and said secondary opening and said outlet opening are adapted to be in flow communication in a second position of said valve means; and
  wherein said valve means is a flexible member having a conically-shaped cross-section and wherein apex on said distal surface of said valve means is operatively positioned adjacent said outlet opening.

* * * * *